(12) United States Patent
Elia et al.

(10) Patent No.: US 11,154,462 B2
(45) Date of Patent: *Oct. 26, 2021

(54) METHOD AND DEVICE OF DETECTING AND/OR BLOCKING REFLUX

(71) Applicant: ART MEDICAL Ltd., Netanya (IL)

(72) Inventors: Liron Elia, Kiryat-Ata (IL); Nir Lilach, M. P. HaAmakim (IL); Eliahu Eliachar, Haifa (IL)

(73) Assignee: ART MEDICAL Ltd., Netanya (IL)

(*) Notice: Subject to any disclaimer, the term of this patent is extended or adjusted under 35 U.S.C. 154(b) by 279 days.

This patent is subject to a terminal disclaimer.

(21) Appl. No.: 16/238,622

(22) Filed: Jan. 3, 2019

(65) Prior Publication Data
US 2019/0133891 A1 May 9, 2019

Related U.S. Application Data

(63) Continuation of application No. 14/986,831, filed on Jan. 4, 2016, now Pat. No. 10,548,816, which is a
(Continued)

(51) Int. Cl.
*A61J 15/00* (2006.01)
*A61B 5/03* (2006.01)
*A61B 5/00* (2006.01)

(52) U.S. Cl.
CPC .......... *A61J 15/0084* (2015.05); *A61B 5/036* (2013.01); *A61B 5/4211* (2013.01);
(Continued)

(58) Field of Classification Search
CPC .. A61J 15/008; A61J 15/0007; A61J 15/0003; A61J 15/0073; A61J 15/0076;
(Continued)

(56) References Cited

U.S. PATENT DOCUMENTS 3,483,859 A 12/1969 Pittman
3,565,079 A 2/1971 Jackson
(Continued)

FOREIGN PATENT DOCUMENTS

CN 1133471 10/1996
EP 0723216 7/1996
(Continued)

OTHER PUBLICATIONS

Advisory Action Before the Filing of an Appeal Brief dated Aug. 26, 2019 From the US Patent and Trademark Office Re. U.S. Appl. No. 14/986,831. (5 pages).
(Continued)

*Primary Examiner* — Tiffany Legette

(57) ABSTRACT

A naso/orogastric device having backflow blocking means and comprises a naso/orogastric tube sized and shaped for being disposed within the esophagus so that at least a distal end thereof being placed in the stomach lumen of a patient, at least one elastic esophageal body, positioned along the naso/orogastric tube, having a pressure dependent volume, at least one esophageal sensor that detects fluid around at least one segment of the naso/orogastric tube, and a pressure regulator that regulates a pressure within the elastic esophageal body according to the detection.

17 Claims, 11 Drawing Sheets

Related U.S. Application Data continuation of application No. 13/575,974, filed as application No. PCT/IL2011/000099 on Jan. 27, 2011, now Pat. No. 9,226,878.

(60) Provisional application No. 61/298,945, filed on Jan. 28, 2010.

(52) U.S. Cl.
CPC .......... *A61B 5/4277* (2013.01); *A61J 15/0003* (2013.01); *A61J 15/0007* (2013.01); *A61J 15/0049* (2013.01); *A61J 15/0073* (2013.01); *A61J 15/0076* (2015.05); *A61J 15/0042* (2013.01)

(58) Field of Classification Search
CPC ............... A61J 15/0049; A61J 15/0042; A61J 15/0084; A61B 5/036; A61B 5/4211
See application file for complete search history.

(56) References Cited

U.S. PATENT DOCUMENTS

| | | | |
|---|---|---|---|
| 3,731,691 | A | 5/1973 | Chen |
| 4,340,046 | A | 7/1982 | Cox |
| 4,384,584 | A | 5/1983 | Chen |
| 4,393,873 | A | 7/1983 | Nawash et al. |
| 4,417,576 | A | 11/1983 | Baran |
| 4,543,089 | A | 9/1985 | Moss |
| 4,735,214 | A | 4/1988 | Berman |
| 4,752,286 | A | 6/1988 | Okada |
| 4,840,173 | A | 6/1989 | Porter, III |
| 5,027,812 | A | 7/1991 | Shapiro et al. |
| 5,067,497 | A | 11/1991 | Greear et al. |
| 5,100,384 | A | 3/1992 | McBrien et al. |
| 5,314,409 | A | 5/1994 | Sarosiek et al. |
| 5,370,656 | A | 12/1994 | Shevel |
| 5,458,568 | A | 10/1995 | Racchini et al. |
| 5,638,813 | A | 6/1997 | Augustine |
| 5,937,861 | A | 8/1999 | Augustine |
| 5,997,503 | A | 12/1999 | Willis et al. |
| 6,277,113 | B1 | 8/2001 | Berube |
| 7,184,827 | B1 | 2/2007 | Edwards |
| 9,226,878 | B2 | 1/2016 | Elia et al. |
| 2001/0053920 | A1 | 12/2001 | Shaker |
| 2002/0111386 | A1 | 8/2002 | Sekins et al. |
| 2004/0034320 | A1 | 2/2004 | Burnett |
| 2004/0220534 | A1 | 11/2004 | Martens et al. |
| 2005/0059965 | A1 | 3/2005 | Eberl et al. |
| 2005/0080832 | A1 | 4/2005 | Stuebe et al. |
| 2005/0245788 | A1 | 11/2005 | Gerber |
| 2007/0044807 | A1 | 3/2007 | Madsen et al. |
| 2007/0282307 | A1 | 12/2007 | Holte |
| 2008/0000482 | A1 | 1/2008 | Maguire et al. |
| 2008/0023005 | A1 | 1/2008 | Tokunaga |
| 2008/0033415 | A1 | 2/2008 | Rieker et al. |
| 2008/0097179 | A1* | 4/2008 | Russo ................. A61B 5/0538 600/343 |
| 2008/0154191 | A1 | 6/2008 | Gobel |
| 2008/0167607 | A1* | 7/2008 | Pfeiffer ................ A61B 5/0538 604/97.01 |
| 2008/0214983 | A1 | 9/2008 | Mauge et al. |
| 2008/0234599 | A1 | 9/2008 | Chiao et al. |
| 2009/0032027 | A1 | 2/2009 | McCachren et al. |
| 2009/0062725 | A1 | 3/2009 | Goebel |
| 2009/0187187 | A1 | 7/2009 | Asirvatham et al. |
| 2010/0016699 | A1* | 1/2010 | Wadhawan ........ A61B 5/14546 600/361 |
| 2010/0249639 | A1 | 9/2010 | Bhatt |
| 2013/0012920 | A1 | 1/2013 | Elia et al. |
| 2013/0014761 | A1 | 1/2013 | Elia et al. |
| 2013/0158514 | A1 | 6/2013 | Elia et al. |
| 2016/0113843 | A1 | 4/2016 | Elia et al. |

FOREIGN PATENT DOCUMENTS

| | | |
|---|---|---|
| JP | 2006-525089 | 11/2006 |
| JP | 2007-500060 | 1/2007 |
| JP | 2008-511362 | 4/2008 |
| JP | 2009-505721 | 2/2009 |
| WO | WO 2004/096330 | 11/2004 |
| WO | WO 2004/105833 | 12/2004 |
| WO | WO 2005/046759 | 5/2005 |
| WO | WO 2006/024825 | 3/2006 |
| WO | WO 2007/024288 | 3/2007 |
| WO | WO 2007/095541 | 8/2007 |
| WO | WO 2008/107872 | 9/2008 |
| WO | WO 2008/154450 | 12/2008 |
| WO | WO 2009/027864 | 3/2009 |
| WO | WO 2009/141598 | 11/2009 |
| WO | WO 2010/016054 | 2/2010 |
| WO | WO 2011/117854 | 9/2011 |

OTHER PUBLICATIONS

Official Action dated Apr. 19, 2019 From the US Patent and Trademark Office Re. U.S. Appl. No. 14/986,831. (23 pages).
Advisory Action and Interview summary dated Aug. 6, 2015 From the US Patent and Trademark Office Re. U.S. Appl. No. 13/575,974.
Advisory Action Before the Filing of an Appeal Brief Dared Nov. 17, 2016 From the US Patent and Trademark Office Re. U.S. Appl. No. 13/635,941. (4pages).
Advisory Action Before the Filing of an Appeal Brief dated Nov. 13, 2015 From the US Patent and Trademark Office Re. U.S. Appl. No. 13/635,941.
Applicant-Initiated Interview Summary dated Nov. 2, 2015 From the US Patent and Trademark Office Re. U.S. Appl. No. 13/635,941.
Applicant-Initiated Interview Summary dated Oct. 3, 2016 From the US Patent and Trademark Office Re. U.S. Appl. No. 13/635,941.
Applicant-Initiated Interview Summary dated Sep. 16, 2016 From the US Patent and Trademark Office Re. U.S. Appl. No. 13/635,949.
Applicant-Initiated Interview Summary dated Jan. 21, 2015 From the US Patent and Trademark Office Re. U.S. Appl. No. 13/575,974.
Applicant-Initiated Interview Summary dated Jul. 21, 2015 From the US Patent and Trademark Office Re. U.S. Appl. No. 13/575,974.
Communication Pursuant to Article 94(3) EPC dated Dec. 1, 2014 From the European Patent Office Re. Application No. 11706361.0.
Communication Pursuant to Article 94(3) EPC dated Jun. 15, 2015 From the European Patent Office Re. Application No. 11706361.0.
Communication Pursuant to Article 94(3) EPC dated Feb. 21, 2017 From the European Patent Office Re. Application No. 11706934.4. (7 Pages).
Communication Pursuant to Article 94(3) EPC dated Jul. 29, 2015 From the European Patent Office Re. Application No. 11706933.6.
Communication Pursuant to Article 94(3) EPC dated Apr. 30, 2014 From the European Patent Office Re. Application No. 11706361.0.
Communication Relating to the Results of the Partial International Search dated Jun. 6, 2011 From the International Searching Authority Re. PCT/IL2011/000101.
Communication Under Rule 164(2)(a) EPC dated Nov. 7, 2016 From the European Patent Office Re. Application No. 11706934.4. (7 Pages).
Communication Under Rule 164(2)(a) EPC dated Mar. 23, 2015 From the European Patent Office Re. Application No. 11706933.6.
International Preliminary Report on Patentability dated Oct. 4, 2012 From the International Bureau of WIPO Re. Application No. PCT/IL2011/000100.
International Preliminary Report on Patentability dated Oct. 4, 2012 From the International Bureau of WIPO Re. Application No. PCT/IL2011/000101.
International Preliminary Report on Patentability dated Aug. 9, 2012 From the International Bureau of WIPO Re. Application No. PCT/IL2011/000099.
International Search Report and the Written Opinion dated May 18, 2011 From the International Searching Authority Re. Application No. PCT/IL2011/000100.

(56) References Cited

OTHER PUBLICATIONS

International Search Report and the Written Opinion dated Jun. 21, 2011 From the International Searching Authority Re. Application No. PCT/IL2011/000099.
International Search Report and the Written Opinion dated Sep. 30, 2011 From the International Searching Authority Re. Application No. PCT/IL2011/000101.
Notice of Allowance dated Oct. 14, 2015 From the US Patent and Trademark Office Re. U.S. Appl. No. 13/575,974.
Notice of Reason for Rejection dated Dec. 2, 2014 From the Japanese Patent Office Re. Application No. 2013-500648 and Its Translation Into English.
Notice of Reason for Rejection dated Jan. 6, 2015 From the Japanese Patent Office Re. Application No. 2012-550569 and Its Translation Into English.
Notification of Office Action and Search Report dated Mar. 11, 2015 From the State Intellectual Property Office of the People's Republic of China Re. Application No. 201180025103.8 and Its Translation Into English.
Notification of Office Action and Search Report dated May 22, 2015 From the State Intellectual Property Office of the People's Republic of China Re. Application No. 201180017052.4 and Its Translation Into English.
Notification of Office Action dated Nov. 2, 2015 From the State Intellectual Property Office of the People's Republic of China Re. Application No. 201180025103.8.
Notification of Office Action dated Nov. 12, 2015 From the State Intellectual Property Office of the People's Republic of China Re. Application No. 201180017052.4 and Its Translation Into English.
Notification of Office Action dated Oct. 15, 2014 From the State Intellectual Property Office of the People's Republic of China Re. Application No. 2011800170524 and Its Translation Into English.
Notification of Office Action dated Jul. 30, 2014 From the State Intellectual Property Office of the People's Republic of China Re. Application No. 201180025103.8 and Its Translation Into English.
Official Action dated Sep. 1, 2016 From the US Patent and Trademark Office Re. U.S. Appl. No. 13/635,941.
Official Action dated Apr. 3, 2017 From the US Patent and Trademark Office Re. U.S. Appl. No. 13/635,941. (28 pages).
Official Action dated Jun. 3, 2016 From the US Patent and Trademark Office Re. U.S. Appl. No. 13/635,949.
Official Action dated Jul. 13, 2015 From the US Patent and Trademark Office Re. U.S. Appl. No. 13/635,941.
Official Action dated Dec. 15, 2015 From the US Patent and Trademark Office Re. U.S. Appl. No. 13/635,949.
Official Action dated Dec. 15, 2016 From the US Patent and Trademark Office Re. U.S. Appl. No. 13/635,949. (26 pages).
Official Action dated Oct. 16, 2017 From the US Patent and Trademark Office Re. U.S. Appl. No. 13/635,949. (27 pages).
Official Action dated Feb. 19, 2016 From the US Patent and Trademark Office Re. U.S. Appl. No. 13/635,941.
Official Action dated Apr. 20, 2015 From the US Patent and Trademark Office Re. U.S. Appl. No. 13/575,974.
Official Action dated Oct. 21, 2014 From the US Patent and Trademark Office Re. U.S. Appl. No. 13/575,974.
Official Action dated Sep. 26, 2018 From the US Patent and Trademark Office Re. U.S. Appl. No. 14/986,831. (47 pages).
Official Action dated Nov. 28, 2014 From the US Patent and Trademark Office Re. U.S. Appl. No. 13/635,941.
Official Decision of Rejection dated Dec. 1, 2015 From the Japanese Patent Office Re. Application No. 2013-500648 and Its Translation Into English.
Patent Examination Report dated Mar. 6, 2015 From the Australian Government, IP Australia Re. Application No. 2011210363.
Patent Examination Report dated Mar. 12, 2015 From the Australian Government, IP Australia Re. Application No. 2011231096.
Requisition by the Examiner dated Nov. 2, 2016 From the Canadian Intellectual Property Office Re. Application No. 2,788,082. (7 Pages).
Requisition by the Examiner dated Jan. 25, 2017 From the Canadian Intellectual Property Office Re. Application No. 2,793,853. (8 Pages).
Restriction Official Action dated Sep. 21, 2015 From the US Patent and Trademark Office Re. U.S. Appl. No. 13/635,949.
Search Report dated Oct. 15, 2014 From the State Intellectual Property Office of the People's Republic of China Re. Application No. 2011800170524 and Its Translation Into English.
Search Report dated Jul. 30, 2014 From the State Intellectual Property Office of the People's Republic of China Re. Application No. 201180025103.8 and Its Translation Into English.
Translation dated Nov. 17, 2015 of Notification of Office Action dated Nov. 2, 2015 From the State intellectual Property Office of the People's Republic of China Re. Application No. 201180025103.8.

\* cited by examiner

METHOD AND DEVICE OF DETECTING AND/OR BLOCKING REFLUX

RELATED APPLICATIONS

This application is a continuation of U.S. patent application Ser. No. 14/986,831 filed on Jan. 4, 2016, which is a continuation of U.S. patent application Ser. No. 13/575,974 filed on Jul. 30, 2012, now U.S. Pat. No. 9,226,878, which is a National Phase of PCT Patent Application No. PCT/IL2011/000099 having International Filing Date of Jan. 27, 2011, which claims the benefit of priority under 35 USC § 119(e) of U.S. Provisional Patent Application No. 61/298,945 filed on Jan. 28, 2010. The contents of the above applications are all incorporated by reference as if fully set forth herein in their entirety.

FIELD AND BACKGROUND OF THE INVENTION

The present invention, in some embodiments thereof, relates to system and method of detecting reflux and, more particularly, but not exclusively, to system and method of detecting reflux when a naso/orogastric tube if placed in esophagus and stomach.

Naso/orogastric feeding, such as esophageal, gastric, duodenal and/or enteral feeding is a form of alimentation and/or metabolic support in which nutrient formulas or medicaments are delivered directly to the gastrointestinal tract, either the stomach or the duodenum. In the majority of cases, nutrient administration is accomplished through use of a tube based device or system, delivering the nutrient through the patient's pharynx and esophagus directly into the stomach, the duodenum or small intestinum (jejunum). One of the difficulties of naso/orogastric feeding is the increased occurrence of reflux-stomach contents going up to the pharynx of the patient.

A common preventive measure against reflux of stomach contents has been to elevate the patient's upper body into a semi-recumbent position (approximately 45°), thereby reducing the ascension of gastric material up the esophagus into the pharynx and lungs.

A number of naso/orogastric tubes have been developed to operate an esophageal balloon seal against gastroesophageal contents ascending from the stomach into the pharynx. For example, U.S. Pat. No. 4,384,584, filed on Oct. 28, 1981 describes a naso-esophageal catheter is provided with an inflatable balloon at its distal end and a signal-emitting device is located within the balloon so that the location of the distal end of the catheter can be determined when it is advanced into the patient's esophagus. After the catheter has been advanced into the patient's esophagus, the balloon is inflated. Thereafter, a trans-cervical esophageal catheter is directed through the patient's neck towards the center of the inflated balloon. After the balloon has been punctured the naso-esophageal catheter is withdrawn and the patient can then be fed with liquid nutrients through the trans-cervical esophageal catheter.

Another example is described in U.S. Patent Application, Publication Number 2009/0062725, filed on Aug. 29, 2007 describes an enteral feeding unit that reduces the occurrence of gastroesophogeal-pharynegal reflux during feeding includes an automatable feeding pump with a feedback sensor for sensing a relative pressure in a patient's stomach and esophagus, and a regulator system for controlling and monitoring feeding rate to the patient as a function of the relative gastro-esophageal pressure. The system includes a stomach probe that provides a fluid-tight closure of the esophagus. The stomach probe includes a tampon-bladder for watertight closure of the esophagus, in which the tampon-bladder is formed of flexible and/or elastic material. At least an inner cavity of the bladder is provided for the reception of a fluid medium. A prescribed pressure for the medium in the tampon-bladder is maintained by an inner lumen forming the stomach probe, from which an outer hose-like lumen extending to the tampon bladder is so arranged that between the outer lumen and the inner lumen a channel is formed connected to the inner cavity of the tampon-bladder arranged on the outer lumen by a number of openings. The inner cavity of the tampon-bladder is connected via a canal formed between the inner and outer lumina with a suitably graded reservoir or equalizing vessel for the liquid medium situated above the tampon-bladder and outside the patient.

SUMMARY OF THE INVENTION

According to some embodiments of the present invention there is provided a naso/orogastric device having backflow blocking means. The naso/orogastric device comprises a naso/orogastric tube sized and shaped for being disposed within the esophagus so that at least a distal end thereof being placed in the stomach lumen of a patient, at least one elastic esophageal body, positioned along the naso/orogastric tube, having a pressure dependent volume, at least one esophageal sensor that detects fluid around at least one segment of the naso/orogastric tube, and a pressure regulator that regulates a pressure within the at least one elastic esophageal body according to the detection.

Optionally, the at least one esophageal sensor comprises at least one impedance sensor for sensing an impedance change around at least one segment of the naso/orogastric tube.

Optionally, the naso/orogastric tube have distal and proximal ends, the at least one esophageal sensor comprises a first esophageal sensor in proximity to the distal end and a second esophageal sensor between the distal end and the proximal end.

More optionally, the pressure regulator regulates the pressure according to difference between a first reading of the first esophageal sensor and a second reading of the second esophageal sensor.

More optionally, the first and second readings are impedance change readings.

More optionally, the pressure regulator regulates the pressure according to the timing of a first detection event of the first reading relative to a second detection event of the second reading.

More optionally, the at least one esophageal sensor comprises at least one impedance sensor for detecting low impedance around the at least one segment.

More optionally, the impedance change is indicative of a content of fluid around the at least one esophageal sensor.

Optionally, the naso/orogastric device further comprises an air conducting tube having a lumen for allowing the pressure regulator to change the pressure in the at least one elastic esophageal body, the air conducting tube being attached to a peripheral surface of the tube.

More optionally, the air conducting tube is made of a layer of biocompatible flexible polymer having a thickness of less than 200 micron.

Optionally, the tube has a first lumen for delivering nutrients, microorganisms, water or medications into the stomach lumen and a second lumen for at least one of inflating and deflating the at least one elastic esophageal body.

More optionally, each the impedance sensor comprises a plurality of electrodes arranged in a circular fashion around the naso/orogastric tube.

Optionally, the naso/orogastric device further comprises a pump assembly, controlled by the pressure regulator so as to regulate the pressure by inflating the at least one elastic esophageal body.

More optionally, the pump assembly comprising an air pressure tank, the pump assembly increases the air pressure in the air pressure tank so as to expedite the inflation.

More optionally, the at least one elastic esophageal body comprises a plurality of balloons arranged one after the other along the naso/orogastric tube.

Optionally, the naso/orogastric device further comprises at least one positioning sensor and a controller that detects a location of at least one portion of the naso/orogastric tube in the esophagus.

More optionally, the at least one positioning sensor comprises a wire threaded in a channel along the naso/orogastric tube, the channel having at least one opening therealong.

More optionally, a pressure assembly regulates the pressure according to the location.

More optionally, the controller detects a movement according to a change in the location; the pressure regulator reducing the pressure in response to the change.

Optionally, the naso/orogastric device further comprises a connection to a cable having a filter to adjust air flow from the pressure regulator.

Optionally, the at least one esophageal sensor comprises a plurality of wires threaded in a plurality of channels along the naso/orogastric tube, each the channel having at least one opening therealong.

According to some embodiments of the present invention there is provided a method of preventing reflux during at least one of tube feeding and esophageal endoscopy of patient. The method comprises disposing a naso/orogastric tube having at least one elastic esophageal body within the esophagus so that at least a distal end thereof being placed in the stomach lumen of a patient and the at least one elastic esophageal body being placed along a segment of esophagus, detecting fluid in at least one region along esophagus in at least position around the naso/orogastric tube, between the segment and the stomach, and regulating a pressure within the at least one elastic esophageal body according to the detection.

Optionally, the detecting comprises sensing an impedance change in the at least one region.

More optionally the regulating comprises increasing the pressure so as to block the esophagus when the impedance is indicative of present of gastric content in the at least position.

More optionally the regulating comprises decreasing the pressure when the impedance is indicative of an absence of gastric content in the at least position.

Optionally, the disposing comprises disposing an elastic stomach body within the stomach, around the distal end, the regulating comprises regulating an additional pressure within the elastic stomach body in parallel and in correspondence with the pressure so as to prevent from the at least one elastic esophageal body from moving toward the pharynx of the patient.

According to some embodiments of the present invention there is provided a naso/orogastric device having backflow blocking means that comprises a naso/orogastric tube having a lumen for delivering content into the stomach lumen of a patient, at least one backflow blocking means positioned along the naso/orogastric tube and a having at least one of a perimeter wider than the perimeter of the naso/orogastric tube and an adjustable structure having at least one state wider than the perimeter of the naso/orogastric tube, and an elastic stomach body at a distal end of the naso/orogastric tube and configured for being inflated by the content so as to have a perimeter wider than the perimeter of the lower esophageal sphincter of the patient.

Optionally, the content comprises a member of a group consisting of: nutrients, microorganisms, water and medications.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
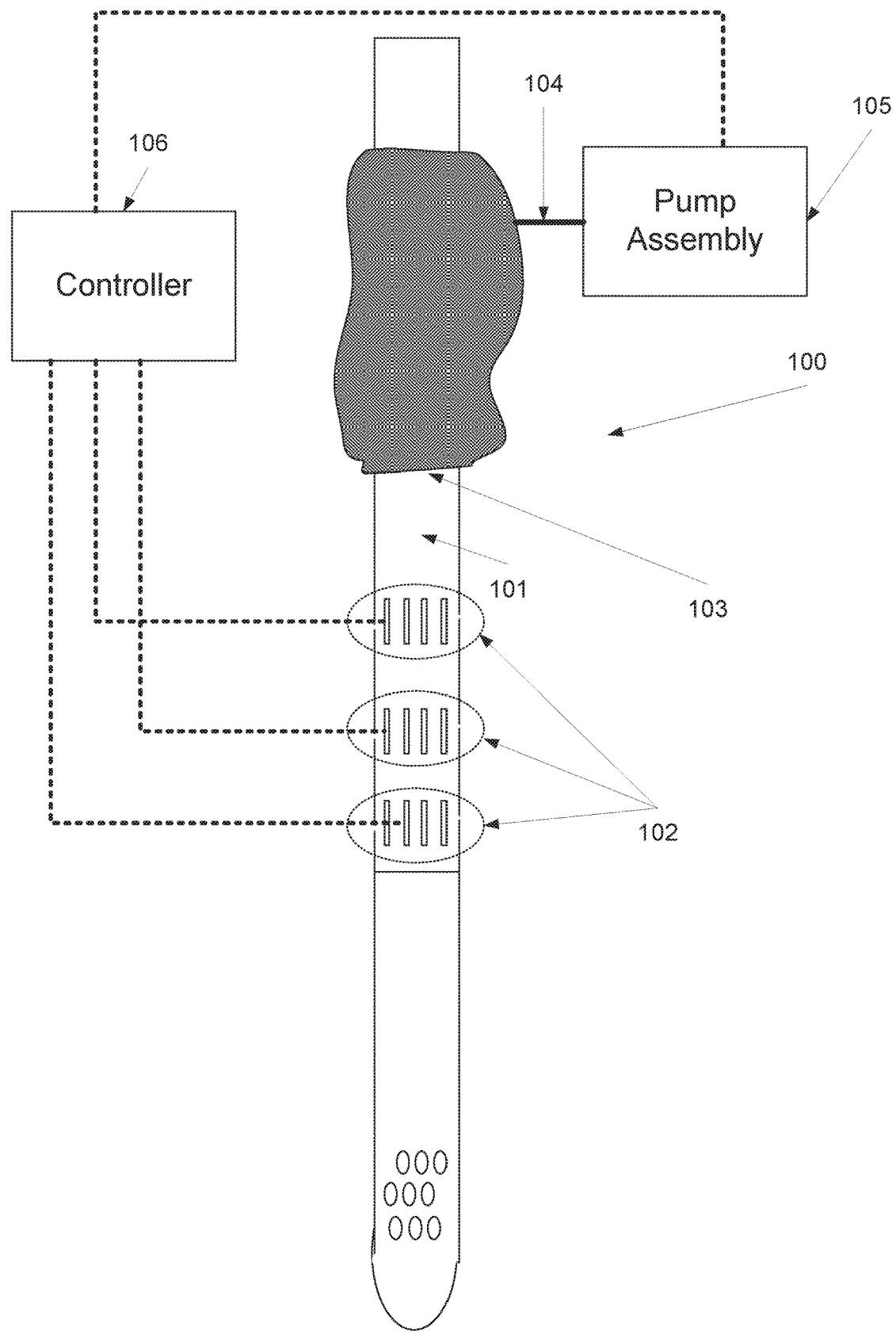
FIG. 1 is a schematic illustration of a portion of a naso/orogastric tube having one or more fluid sensors for detecting a reflux and a controllable reflux blocking device for blocking GI contents, according to some embodiments of the present invention.

The present invention, in some embodiments thereof, relates to system and method of detecting reflux and, more particularly, but not exclusively, to system and method of detecting reflux when a naso/orogastric tube if placed in esophagus and stomach.

According to some embodiments of the present invention there is provided a naso/orogastric device having backflow blocking means which are operated according to the detection of fluids in the esophagus and or around the Lower Esophageal Sphincter (LES), for example using impedance sensors. The naso/orogastric device includes a naso/orogastric tube sized and shaped for being disposed within the esophagus so that at least a distal end thereof is placed in the stomach lumen of a patient. Such a naso/orogastric tube may be used for tube feeding and/or esophageal endoscopy. The naso/orogastric device further includes one or more esophageal elastic bodies, such as balloons which are positioned along the naso/orogastric tube and have a pressure dependent volume and one or more esophageal and or LES sensors that detect, in use, fluids in around segments of the naso/orogastric tube in the esophagus and or LES. The fluid sensors are connected to a pressure regulator that regulates the pressure within the elastic esophageal body according to the detection of fluid. For example, the pressure regulator operates a pump assembly according to the detection.

Optionally, the fluid sensors are impedance sensors each includes one or more electrodes, such as annular electrodes, helical electrodes, and/or strip electrodes.

According to some embodiments of the present invention, there is provided a naso/orogastric device having naso/orogastric tube and backflow blocking means, such as a balloon, which is connected to a flexible air conducting tube attached to the peripheral surface of the naso/orogastric tube. Optionally, the conducting tube is part of a flexible sheath covering the naso/orogastric tube. The flexible sheath has a thickness of between about 50 and about 150 micron and designed to shriek on to the peripheral surface of the naso/orogastric tube thus not causing further discomfort to the patient when passing through the nasopharynx. As the flexible air conducting tube is widen only when being used for inflating the backflow blocking means and as the perimeter of the naso/orogastric tube can be reduced as an outcome of the extraction of the flexible air conducting tube from its inner lumen, such a naso/orogastric device apply less pressure on the esophagus's walls when disposed therein than a naso/orogastric device in which the air conducting tube in placed in the inner lumen. When using such a flexible sheath side effects of using a large bore tube, for example discomfort is avoided.

According to some embodiments of the present invention there is provided a naso/orogastric device having backflow blocking means and an elastic stomach body which is designed to be inflated in the stomach so as to prevent the sliding of the backflow blocking means toward the pharynx. The naso/orogastric device has a naso/orogastric tube having a lumen for delivering content, such as nutrients, microorganisms, water and/or medications, into the stomach lumen of a patient, a backflow blocking means, such as one or more balloons positioned along the naso/orogastric tube and a having a perimeter wider than the perimeter of the naso/orogastric tube or an adjustable structure having a state wider than the perimeter of the naso/orogastric tube. The naso/orogastric device further includes an elastic stomach body having a pressure dependent volume at a distal end of the naso/orogastric tube. Optionally, the elastic stomach body is inflated by the delivered content so as to have a perimeter wider than the perimeter of the lower esophageal sphincter of the patient. In such a manner, the naso/orogastric tube does not slide outward the body of patient and therefore does not elevate the backflow blocking means toward the pharynx.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a portion of a naso/orogastric device 100 having a naso/orogastric tube 101 one or more fluid sensors 102 for detecting a reflux of GI contents, which may be referred to herein as backflow, and a controllable reflux blocking device 103 for blocking GI contents, according to some embodiments of the present invention.

The naso/orogastric device 100 includes a naso/orogastric tube 101 having an inner lumen (not shown) for delivering nutrients, microorganisms, water and/or medications. The naso/orogastric tube 101 is defined herein as any commonly used naso/orogastric tube, for example a naso/orogastric feeding tube, a naso-esophageal catheter, a gastric feeding tube, such as a nasogastric feeding tube, a duodenal feeding tube and an enteral feeding tube. The naso/orogastric tube 101 is sized and shaped for being disposed within the esophagus so that a distal end thereof is placed in the stomach lumen of a patient. Optionally, the naso/orogastric tube 101 comprises a small diameter flexible tube preferably made of transparent plastic, such as polyvinyl Chloride or silicone. The length of the naso/orogastric tube 101 is adjusted to the size of the patient. For example, a naso/orogastric device for adult patients has a naso/orogastric tube 101 of more than 120 centimeter long for 18 Fr tube and a naso/orogastric device for infants has a naso/orogastric tube 101 of more than 40 centimeter long for 5 Fr tube.

As outlined above, the naso/orogastric device 100 further comprises one or more fluid sensors 102 for detecting at least the presence or absence of fluids, such as impedance sensors and/or optical sensors, along the naso/orogastric tube 101. In use, when placed in the esophagus, the fluid sensors 102 detect presence or absence of a gastric contents backflow, for example as described below.

The controllable reflux blocking device 103 includes one or more esophageal elastic bodies such as balloon catheters, which are positioned along the naso/orogastric tube and has a pressure dependent volume. For brevity, the one or more esophageal elastic bodies are referred to herein as an elastic esophageal body 103. The elastic esophageal body 103 is connected to a distal end of an air conducting tube 104 that allows inflating the elastic esophageal body 103. The proximal end of the air conducting tube 104 is optionally connected to a pump assembly 105 that inflates the elastic esophageal body 103. Optionally, the elastic esophageal body 103, which is connected to the conducting tube, is connected to pressure tank that releases the pressure in high speed, using controller 106, and inflate the balloon in high speed, for example as further described below. Optionally, the elastic esophageal body 103 is connected to another air conducting tube that allows deflating the elastic esophageal body 103. Optionally, the pump assembly 105 is a bidirectional pump that allows inflating and deflating the elastic esophageal body 103.

The one or more fluid sensors 102 and the pump assembly 105 are connected to a controller 106. The controller 106, which may include a pressure regulator module, operates the pump assembly 105 according to the reading of the fluid sensors 102.

Figure 2A:
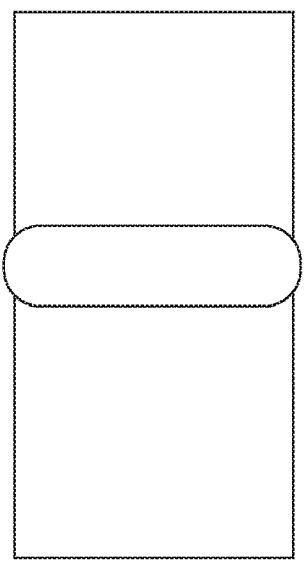
FIGS. 2A-2C are exemplary electrodes of exemplary impedance sensors, according to some embodiments of the present invention.
Figure 2B:
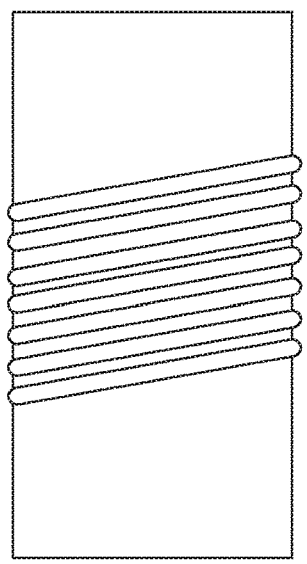

As described above the fluid sensors 102 may be impedance sensors 102. Optionally, each impedance sensors 102 includes one or more electrodes that encircle the naso/orogastric tube 101. Optionally, each impedance sensor 102 includes one or more annular or helical electrodes, for example as shown at FIGS. 2A and 2B.

Figure 2C:
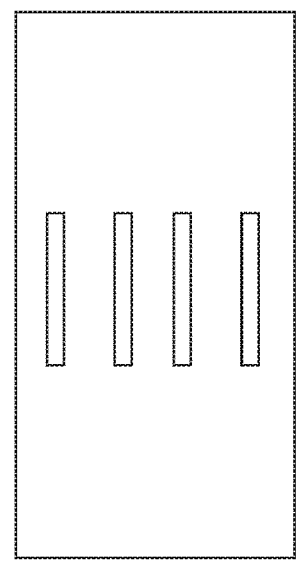

Optionally, each impedance sensors 102 includes a plurality of parallel strip electrodes which are circularly and dividedly placed around a common segment of the naso/orogastric tube 101, for example as shown at FIG. 2C. Optionally, each electrode covers an area of about 1 mm$^2$ and 150 mm$^2$. Optionally, between 2 and 20 electrodes are used in each impedance sensor 102. Optionally, the distance between each pair of parallel electrodes is between about 3 mm and about 30 mm.

Optionally, the electrode is made of steel, stainless steel, brass, copper, platinum, silver, gold, aluminum alloy, zinc, nickel, tin, magnesium alloy, bronze, phosphor bronze, conductive polymers and/or any composition thereof and/or any alloy therefrom.

Optionally, the electrodes are printed on the peripheral surface of the naso/orogastric tube 101. Optionally, the electrodes are coated with Gold, Silver, Nickel, Zinc, Tin, Copper and/or any composition thereof and/or any alloy therefrom.

Optionally, the electrodes are shaped as Circular, rectangular, and/or triangular spots.

Optionally, one or more of the fluid sensors 102 are placed so as to detect fluid in the stomach, for example in proximity to the lower esophageal sphincter. In such a manner, reflux may be detected even before the GI contents arrive at the esophagus.

Figure 2D:
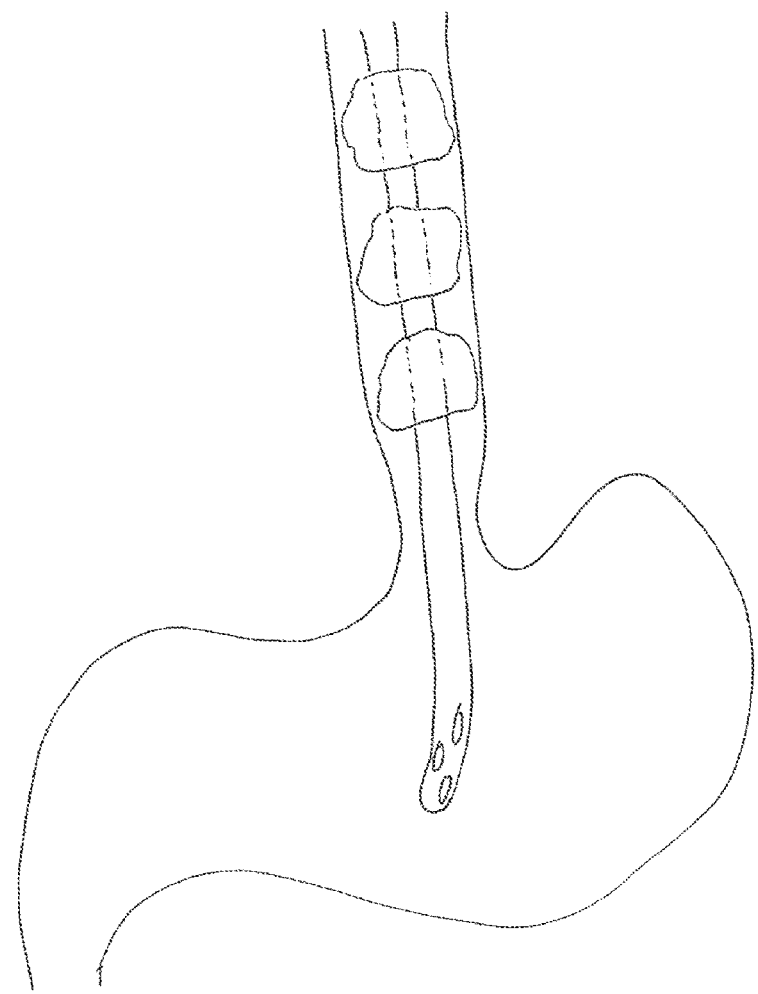
FIG. 2D is a schematic illustration of a portion of a naso/orogastric tube having a plurality of balloons for blocking backflow, according to some embodiments of the present invention.

Optionally, as outlined above and depicted in FIG. 2D, the elastic esophageal body 103 includes several balloons. In such a manner, the balloons may be in a lower pressure, placing lower pressure on the esophagus. If the GI contents pass the first balloon they are stopped by the second balloon. The space between the balloons traps the gastric content backflow without applying substantial pressure on the esophageal walls.

Figure 3:
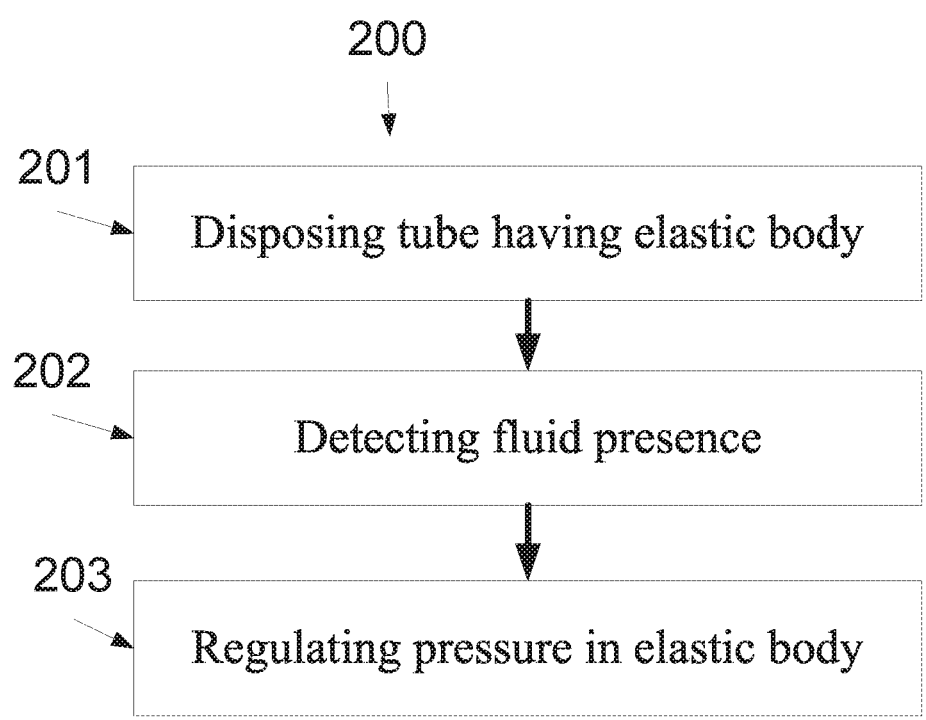
FIG. 3 is a flowchart of a method of blocking reflux when a naso/orogastric device is temporary disposed in the esophagus, according to some embodiments of the present invention.

Reference is now also made to FIG. 3, which is a flowchart of a method of blocking reflux when a naso/orogastric device is temporary disposed in the esophagus, according to some embodiments of the present invention.

First, as shown at 201, a naso/orogastric tube with an elastic esophageal body, such as shown at 101, 103, is disposed in the esophagus so that at least a distal end thereof is in the stomach lumen of a patient and the elastic esophageal body is placed in a certain segment of esophagus. In such a manner, the naso/orogastric tube may be used for delivering nutrients, microorganisms, water and/or medications, as outlined above.

Now, as shown at 202, the presence or the absence of GI contents in the esophagus is sensed, for example by the one or more fluid sensors 102. Optionally, the fluid sensors 102 are impedance sensors that sense an impedance change in at least one region along esophagus, in a around the naso/orogastric tube 101, between the stomach and the elastic esophageal body 103. The detection of GI contents in the esophagus, for example the detection of impedance change, is indicative of GI contents backflow. The measurements of the fluid sensors 102 are forwarded to the controller 106.

As shown at 203, the controller 106 regulates the pressure within the elastic esophageal body 103 according to the detected gastric content in the esophagus, for example according to a detected impedance change.

Optionally, the pressure regulator module performs such regulation to allow inflating the elastic esophageal body 103 in response to the detection of gastric contents in the esophagus and/or surrounding the LES. Optionally, the elastic esophageal body 103 is maintained in low pressure when gastric contents are not detected in the esophagus. In such a manner, no redundant pressure is applied on the esophageal walls while the naso/orogastric device 100 is used for feeding and/or diagnosing the patient. By avoiding the appliance of redundant pressure on the esophageal walls, Esophageal ulcer and other disorders may be avoided.

According to some embodiments of the present invention, the one or more fluid sensors 102 detect the direction of fluids in the esophagus. For example, the controller 106 may regulate the pressure using its pressure regulator in the elastic esophageal body 103 according to the timing of a first detection event, such as a detection of a first impedance change by a first fluid sensor 102 relative to a second detection event, such as a detection of a second impedance change by a second fluid sensor 102. If the first fluid sensor is closer to the stomach than the second fluid sensor and optionally time between the first and the second detection events is in a predefined range, the reading of the fluid sensors 102 are indicative of the direction of fluids in the esophagus.

According to some embodiments of the present invention, the controller 106 analyses the content of fluid according to the measurements of the fluid sensors 102. For example, different impedance may be indicative of different compositions of the fluid around the fluid sensors 102. For example, while one impedance value and/or range of impedance values is indicative of saliva, another impedance value and/or range of impedance values is indicative of gastric content. For example, while gastric content has a high conductivity and respectively low impedance, air has a low conductivity and respectively high impedance.

Figure 4:
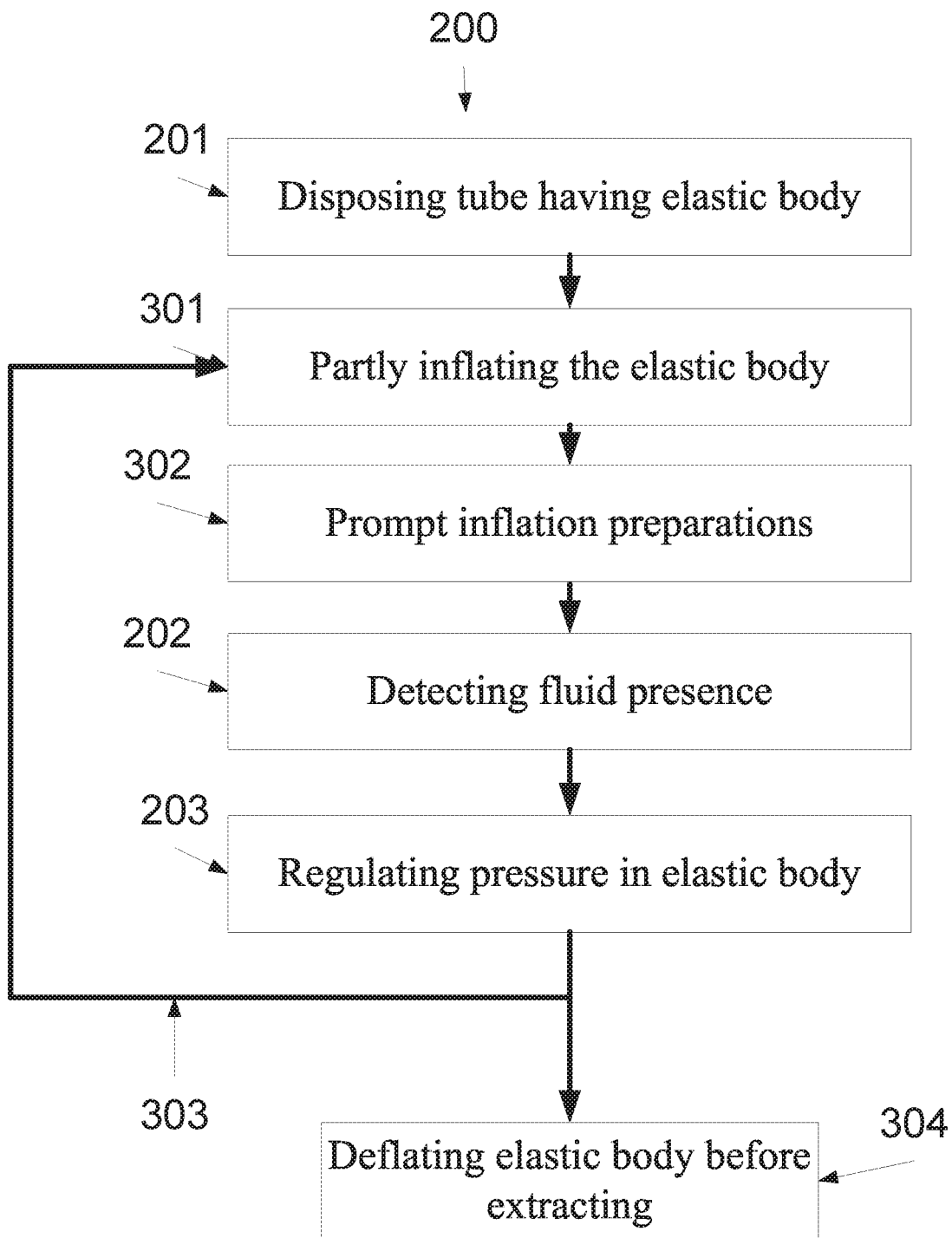
FIG. 4 is a flowchart of a method of blocking reflux when a naso/orogastric device is temporary disposed in the esophagus, according to some embodiments of the present invention.

Reference is now also made to FIG. 4, which is a flowchart of a method of blocking reflux when a naso/ orogastric device is temporary disposed in the esophagus, according to some embodiments of the present invention. Blocks 201-203 are as depicted in FIG. 3. However, a number of additional operations are depicted in FIG. 4.

Optionally, as shown at 301, after the naso/orogastric tube 101 is disposed in the esophagus, the elastic esophageal body 103 is partly inflated, for example about three quarters at a predetermined value. Optionally, the pump assembly 105 is used for inflating the elastic esophageal body 103. Optionally, the inflation is performed until a minor pressure, for example between about 10 mmHg (Torr) and about 40 mmHg is detected by a pressure sensor, for example pressure sensor 402 in FIG. 5.

Optionally, the minimum diameter of the elastic esophageal body 103 is as the inner diameter max value of the lower esophageal sphincter so as to prevent from slipping into the stomach or up the pharynx and or for prevent gastric reflux to overtake the elastic esophageal body.

Optionally, as shown at 302, after the naso/orogastric tube 101 is disposed in the esophagus, the pump assembly 105 is prepared for a prompt inflation, optionally with a pressure tank, of the elastic esophageal body 103.

Figure 5:
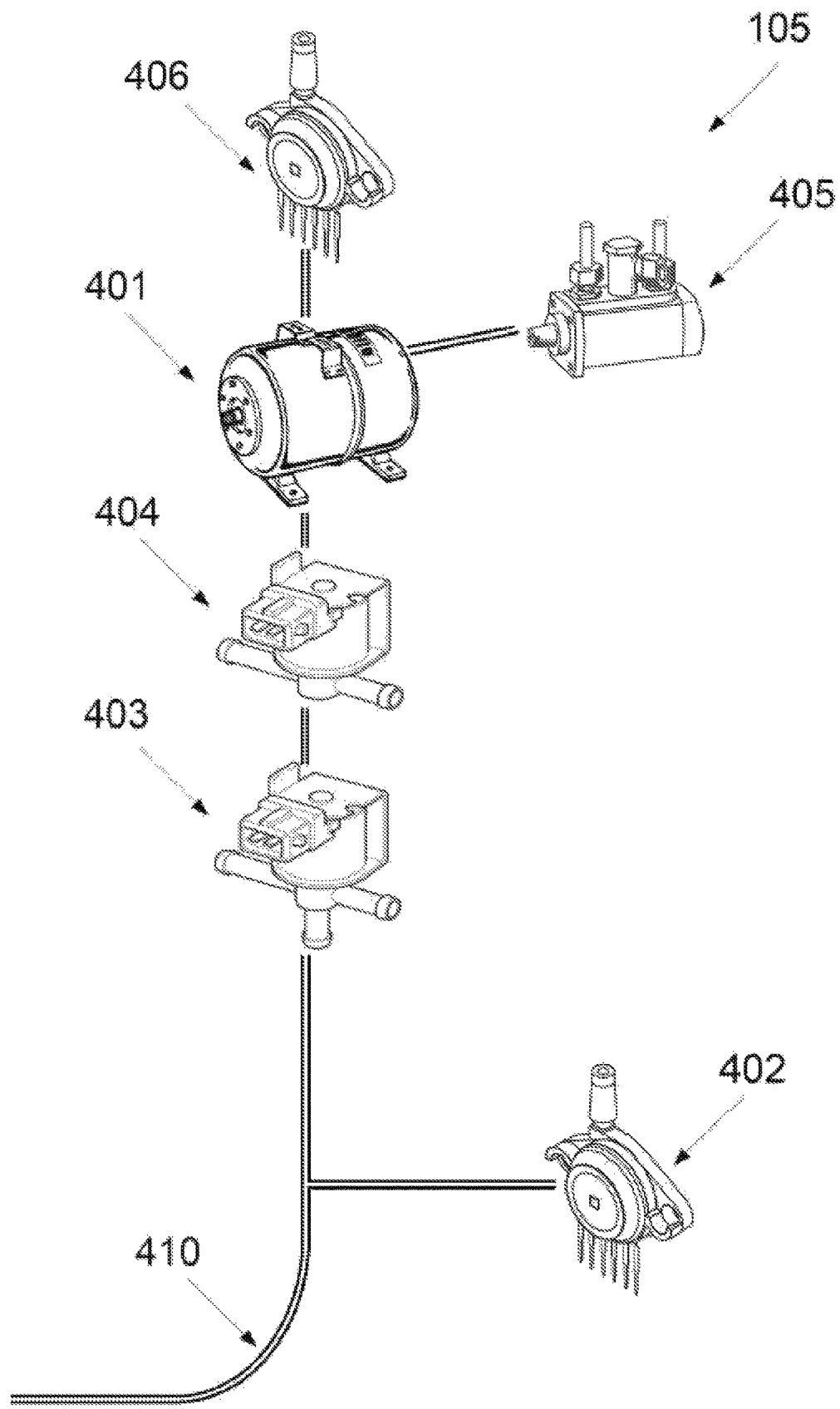
FIG. 5 which is a schematic illustration of an exemplary pump assembly, according to some embodiments of the present invention.

Reference is now also made to FIG. 5, which is a schematic illustration of an exemplary pump assembly 105 which is connected, via an air conducting tube 410, to the elastic esophageal body 103, according to some embodiments of the present invention. Optionally, the pump assembly 105 includes an air container 401, which may be referred to herein as a pressure tank 401, a pressure sensor 402 for estimating the pressure implemented on the elastic esophageal body 103 by esophagus, a valve 403, such as a three ways valve, for diverting air from the air pressure tank 401 either to the elastic esophageal body 103 or outside the naso/orogastric device 100, also used to deflate the Balloon, an inflation release valve 404 for controlling the pressure maintenance inside 401 and for controlling the inflation of the Balloon. Optionally, the controller 106 controls the valves 403, 404 and the pump 405 and receives data from the sensors 402, 406.

In use, for example in 302, the pump assembly 105 increases the pressure in the air container 401 optionally to achieve a predefined pressure according to the reading of the pressure sensor 406. The built pressure allows prompt inflation of the elastic esophageal body 103. Optionally, the valve 403 allows reducing the pressure in the elastic esophageal body 103 so as to avoid creating esophageal ulcer.

When a reflux is identified, for example according to the identification of a backflow as shown at 202-203, the elastic esophageal body 103 is inflated, for example by the air from the air container 401. As the pressure in the air container 401 is high, for example 300 mmHg or more, the elastic esophageal body 103 may be inflated in less than a second.

As shown at 303, this process depicted in blocks 301-302 and 202-203 may be repeated as long as the naso/orogastric tube 101 is in the esophagus, for example during one or more tube feeding sessions.

Now, as shown at 304, the elastic esophageal body 103 is deflated before the naso/orogastric device 100 is extracted from the esophagus of the patient. Optionally, the air is released by opening the valve 403, or by using pump assembly 105 as suction pump for the Balloon deflation.

Figure 6:
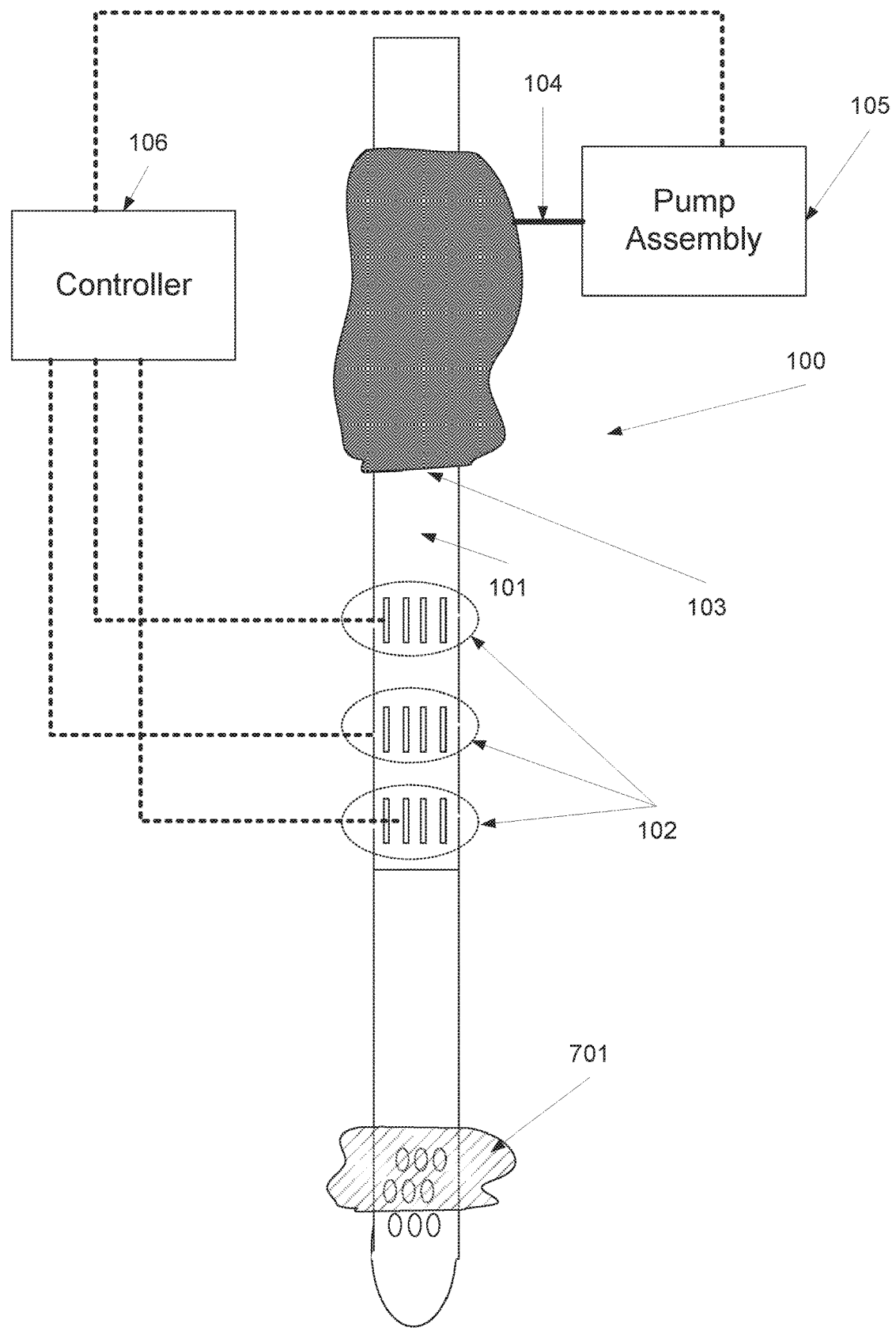
FIG. 6 is a schematic illustration of a portion of the naso/orogastric device depicted in FIG. 1, where an elastic stomach body 701 is attached to the distal end of its naso/orogastric tube, according to some embodiments of the present invention 101.

Reference is now made to FIG. 6 which is a schematic illustration of the naso/orogastric device 100 depicted in FIG. 1, where an elastic stomach body 701 is attached to the distal end of its naso/orogastric tube 101, according to some embodiments of the present invention. In use, the distal end and the elastic stomach body 701 are placed in the stomach of the patient. The elastic stomach body 701 is connected, via an inflation tube, and optionally deflation tube, to the pumping assembly 105 and/or to another pump. In use, the elastic stomach body 701 is inflated in the stomach. In such a manner, the elastic stomach body 701 prevents from the naso/orogastric tube 101 to slide toward the pharynx. This prevents from the elastic esophageal body 103 to slide toward the Lower pharynx, a location in which it can block the trachea and choke the patient.

As described above, the naso/orogastric tube 101 may be a naso/orogastric feeding tube 101. In such an embodiment, the elastic stomach body 701 may be placed on top of one or more of the feeding apertures of the naso/orogastric tube 101. In use, the feeding apertures are placed in the stomach so as to allow the feeding of the patient. In use, the elastic stomach body 701 is filled by the feeding contents, for example feeding fluids. The feeding contents are accumulated in the elastic stomach body 701, increasing its volume so that its diameter is larger than the diameter of the lower esophageal sphincter. Optionally, the elastic stomach body 701 has one or more apertures through which the feeding contents are released. The apertures are optionally widened with the increase in the volume of the elastic stomach body 701. In such a manner, the elastic stomach body 701 is filled before the feeding contents are released.

Optionally, the elastic stomach body 701, when full, is used as an anchor for the naso/orogastric feeding tube 101. The weight of the filled elastic stomach body 701 limits the movement of the naso/orogastric feeding tube 101 and prevents it from fold and/or being bundled in the stomach, and if there are sensors in the stomach they are submerged within the stomach content. In such a manner, the fluid sensors 102 and elastic esophageal body 103 do not sink toward the stomach or up the esophagus and remain in the esophagus so as to allow proper functioning as described above.

Figure 7:
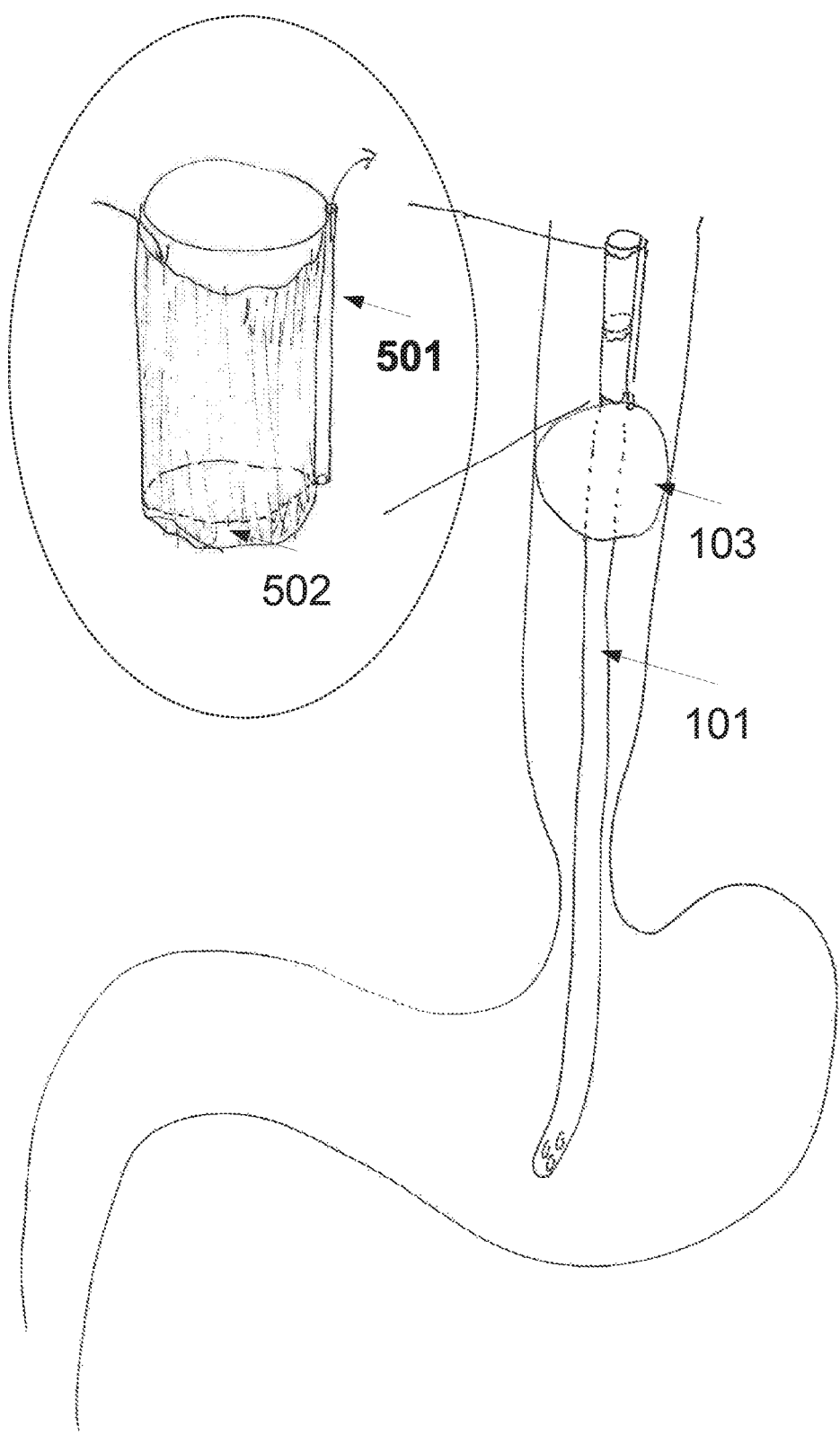
FIG. 7 is a schematic illustration of a portion of a naso/orogastric tube having an external air conducting tube for inflating an elastic esophageal body thereof, according to some embodiments of the present invention.

According to some embodiments of the present invention, the elastic esophageal body 103 is inflated by a flexible air conducting tube is located outside the lumen of the naso/orogastric tube 101, for example attached on the peripheral surface thereof. In such an embodiment, the perimeter of the naso/orogastric tube 101 may be reduced as it does not have to contain a conducting lumen for conducting air for inflating the elastic esophageal body 103. It should be noted that as the elastic esophageal body 103 should be inflated relatively fast in order to block the backflow, the perimeter of the conducting lumen has to be relatively wide, for example having a diameter of more than 1 mm and therefore the extraction thereof from the naso/orogastric tube 101 has a substantial effect on the perimeter of the naso/orogastric tube 101. For example, reference is now made to FIG. 7, which is a schematic illustration of a naso/orogastric tube 101 and a blowup of segment thereof that depicts an external air conducting tube 501 for inflating the elastic esophageal body 103, according to some embodiments of the present invention. As the external air conducting tube 501 is used only when the elastic esophageal body 103 is inflated, namely a short period of no more than few seconds, it is mostly in an uninflated state, adding practically nothing to the perimeter of the naso/orogastric tube 101. Optionally, the external air conducting tube 501 is made of a thin polymeric layer, optionally about 80 micron or less. Optionally, the external air conducting tube 501 is part of a sheath 502 which is put on the naso/orogastric tube 101. It should be noted that the naso/orogastric tube 101 may contain an air extraction lumen for removing air from the elastic esophageal body 103. However, as such a lumen may be relatively thin, for example with a diameter of less than 1 mm, the perimeter of the naso/orogastric tube 101 may be relatively limited.

Figure 8:
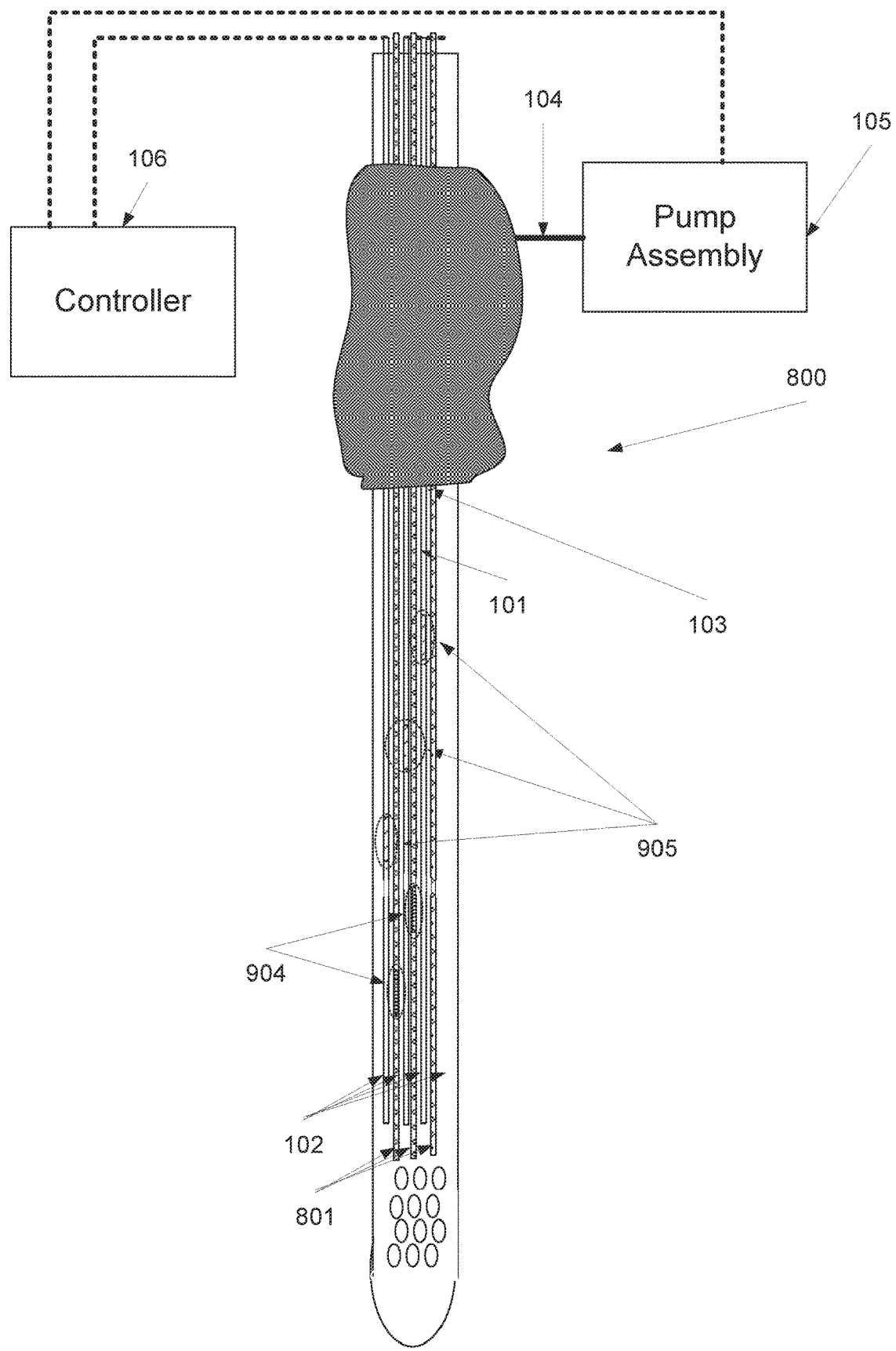
FIG. 8 is a schematic illustration of a naso/orogastric device, such as the naso/orogastric device depicted in FIG. 1, where one or more positioning sensors are placed along the naso/orogastric tube of the device, according to some embodiments of the present invention.
Figure 9A:
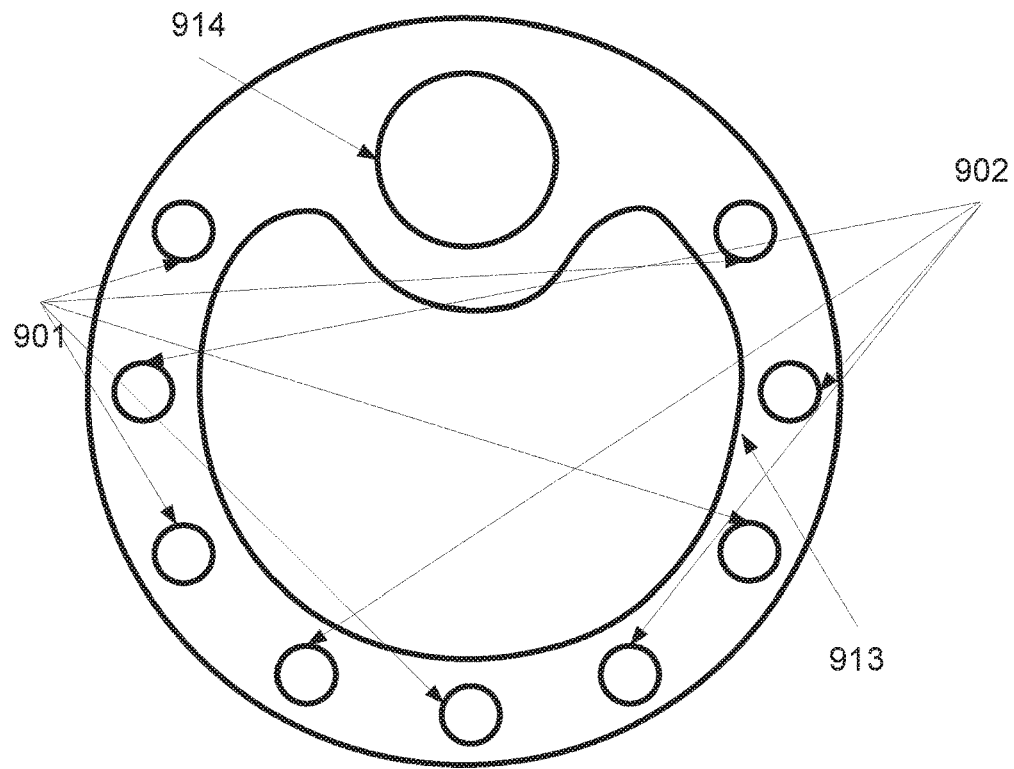
FIG. 9A is a cross sectional illustration of an exemplary naso/orogastric tube, according to some embodiments of the present invention.
Figure 9B:
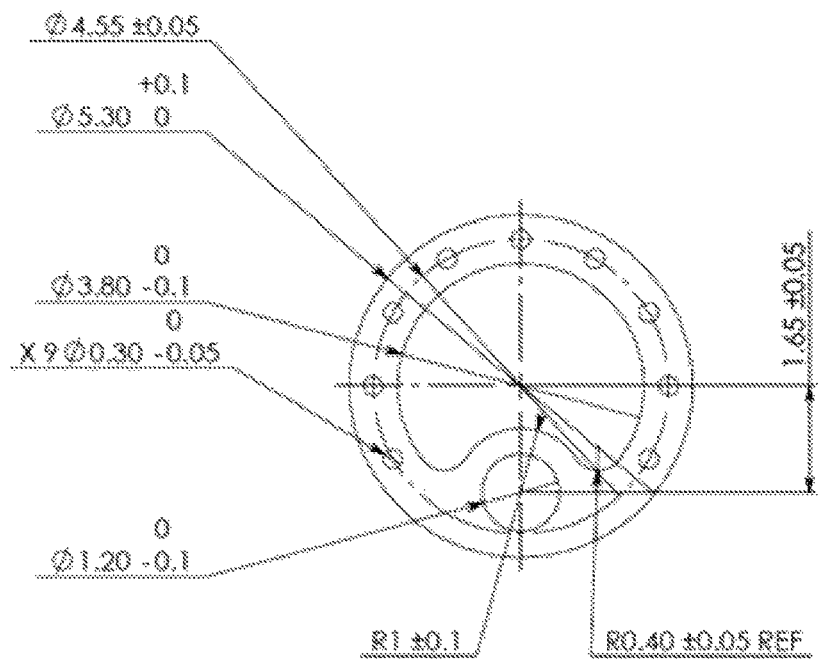
FIG. 9B is a cross sectional illustration of an exemplary naso/orogastric tube, with exemplary dimensions, according to some embodiments of the present invention.
Figure 9C:
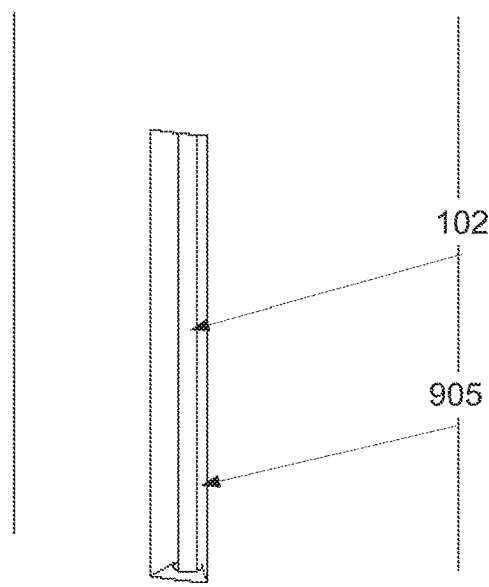
FIGS. 9C and 9D are exemplary openings for allowing a fluid sensor and a positioning sensor to function, according to some embodiments of the present.

Reference is now made to FIG. 8 which is a schematic illustration of a naso/orogastric device 800, such as the naso/orogastric device 100 depicted in FIG. 1, a plurality of wires of an exemplary positioning sensor 801 are placed along the naso/orogastric tube 101, according to some embodiments of the present invention. In this naso/orogastric device 800, the positioning sensor 801 and the fluid sensor include wires which are threaded in the naso/orogastric tube 101, for example in channels which are formed therein. For example, FIG. 9A is a cross sectional illustration of an exemplary naso/orogastric tube having channels 901 for positioning wires of positioning sensor 801 and channels 902 for the wires of the fluid sensor 102, which are optionally, as the wires of the positioning sensor 801, threaded along the naso/orogastric tube 101. FIG. 9B is a sectional schematic illustration depicting optional and exemplary dimensions of such an exemplary naso/orogastric tube. In order to allow the sensors 801, 102 to detect changes in the intrabody surrounding, for example in the esophageal lumen, openings 904, 905, such as cuts, optionally longitudinal, are formed in one or more locations along the channels, optionally in different heights. In use, for the wires of the fluid sensor 102, the openings 905 allow a direct contact with GI fluid in the esophageal lumen. The direct contact allows detecting impedance change between different segments of the naso/orogastric tube 101. Optionally, the wires of the fluid sensor 102 are immersed in the naso/orogastric tube 101 so that a direct contact is formed when the GI fluids pass via the openings 905. For example, FIG. 9C depicts an exemplary immersed fluid sensor 102. In this example, a segment of a wire of the fluid sensor 102 remains in the channel, below the opening. In such a manner, the wires of the fluid sensor 102 are not affected and/or blocked by the inner walls of the esophagus, for example with the esophageal sphincter.

Figure 9D:
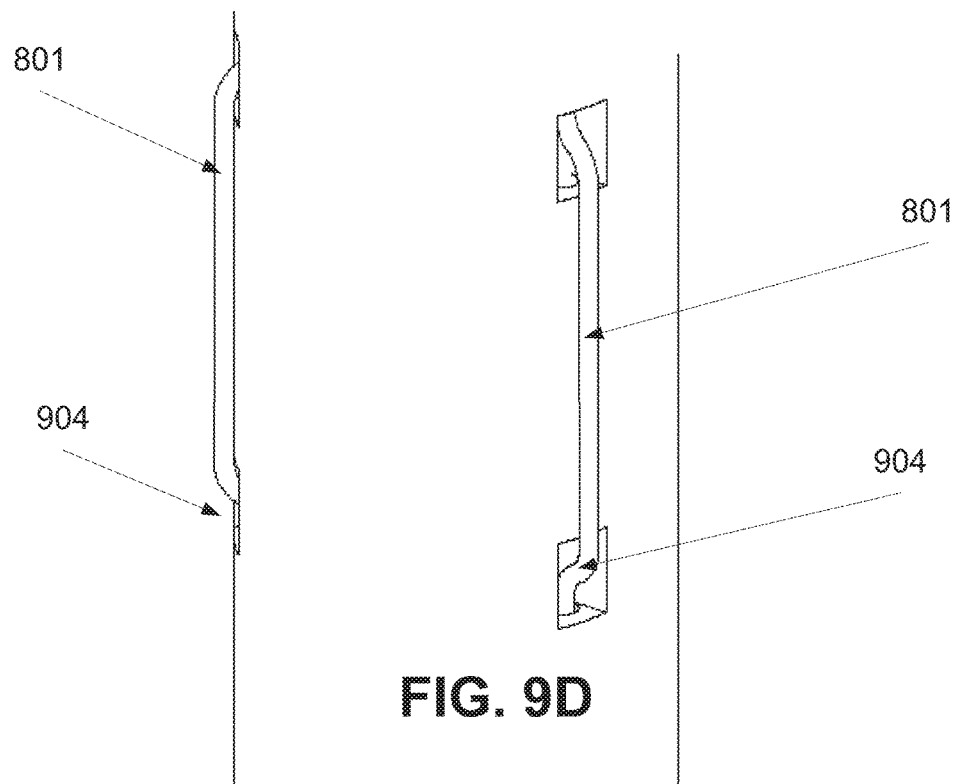

In use, for the wires of the positioning sensor 801, the openings 904 allow a direct contact with inner walls of the esophagus, for example with the esophageal sphincter. The direct contact allows detecting impedance level, impedance change, and/or movement around at one or more segments of the naso/orogastric tube 101. Optionally, the positioning sensor 801 detects and monitors position as described in International Patent Application No. WO2008/107872, Published on Sep. 12, 2008, which is incorporated herein by reference. Optionally, the wires of the positioning sensor 801 are extracted via the openings 904 to protrude above the surface of the naso/orogastric tube 101. In this example, a segment of a wire of the positioning sensor 801 is extracted, via the opening 904, from its channel. In another example, depicted in FIG. 9D, the wire is treaded via holes in the naso/orogastric tube 101. In such a manner, segments of the wire of the positioning sensor 801 are above the naso/orogastric tube 101 and other segments are below the naso/orogastric tube 101. In such a manner, a direct contact with the inner walls of the esophagus, for example with the esophageal sphincter, may be established.

Optionally, the wires of the positioning sensors 801 are used to position the naso/orogastric tube 101 in the esophagus, for example as described in International Patent Application No. WO2008/107872, published on Sep. 12, 2008, which is incorporated herein by reference.

According to some embodiments of the present invention, the wires of the positioning sensor 801 are connected to and controlled by the controller 106. Optionally, the controller 106 monitors changes in the positioning of the naso/orogastric tube 101 according to the reading of the impedance in the wires positioning sensors 801. As each wire may be exposed by an opening that is formed on another height of the naso/orogastric tube 101, a change in the impedance in each wire indicates that a contact is established with the lumens' wall, for example at the esophageal sphincter. This allows estimating the location of the naso/orogastric tube 101.

In such embodiments, the pressure inside the elastic esophageal body 103 is adjusted according to changes in the positioning of the naso/orogastric tube 101.

Optionally, the position of the naso/orogastric tube 101 is monitored to detect misplacement and/or an unwanted displacement. In such a manner, the controller 106 may instruct the pump assembly 105 to reduce the pressure inside the elastic esophageal body 103 when misplacement and/or an unwanted displacement are detected. This may be used as a safety mechanism that assure that if the patient tries to extract the naso/orogastric device 100, when the elastic esophageal body 103 is fully and/or semi inflated, the pressure in the elastic esophageal body 103 is reduced, optionally immediacy, for example within less than a second.

As described above, the naso/orogastric tube 101 is set to conduct content into the stomach lumen of a patient and air to the elastic esophageal body 103. In such an embodiment, the naso/orogastric tube 101 includes both a first channel orifice 913 for conducting content, such as feeding, and a second channel orifice 914 for conducting air to the elastic esophageal body 103.

Figure 10B:
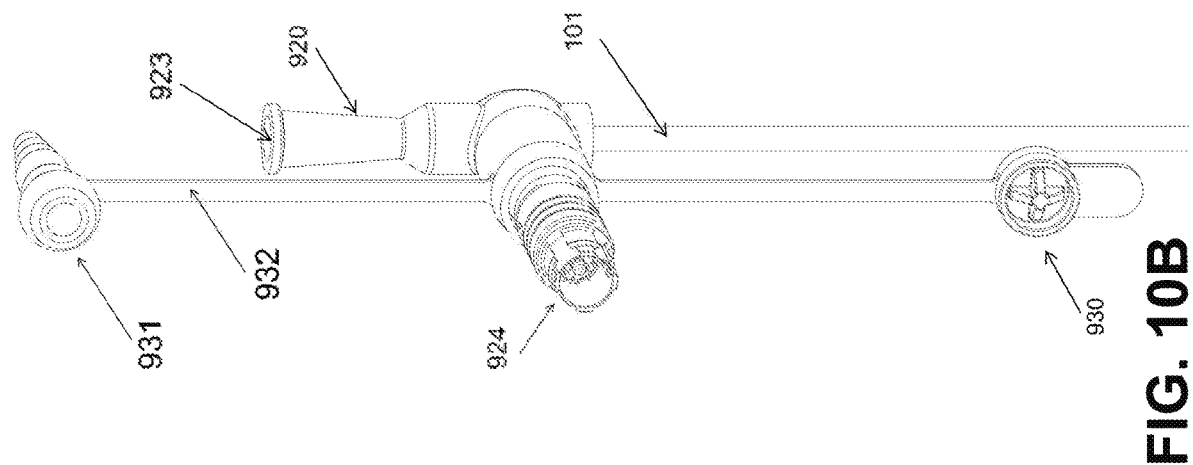
FIGS. 10A and 10B are schematic illustrations of an exemplary connector that allows connecting a naso/orogastric tube to a feeding device, a pump assembly and a controller, according to some embodiments of the present invention.
Figure 10A:
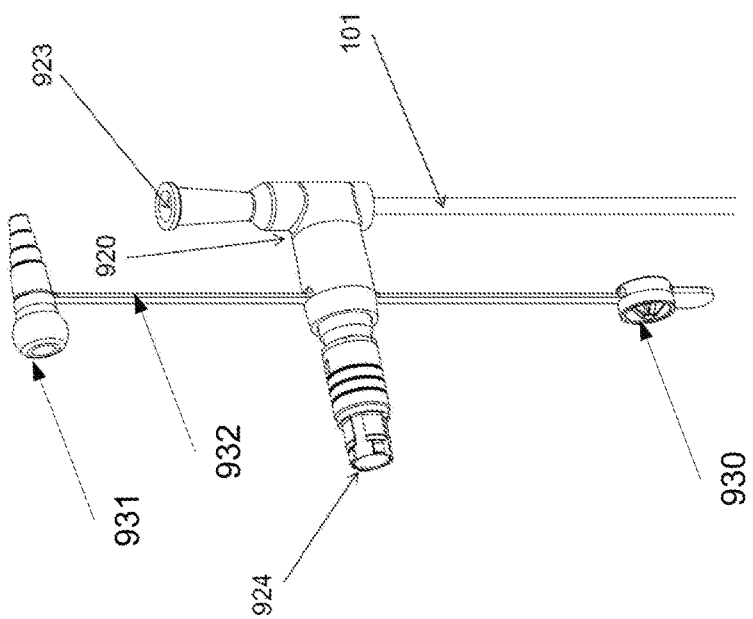

Reference is now also made to FIGS. 10A and 10B which schematically an exemplary connector 920 that allows connecting the naso/orogastric tube 101 to a feeding device and to a pump assembly and a controller, such as 105 and 106, according to some embodiments of the present invention. The connector 920 has a first channel orifice 923 for connecting a feeding device for conducting content via the first channel 913 and a second channel orifice 924 for connecting the pump assembly 105 for conducting air via the second channel 914 and optionally for connecting the controller 106 to the sensors in channels 901 and 902.

Optionally, the second channel orifice 924 is connected to the channels 901, 902 that accommodate the sensors 102, 801. In such a manner, the naso/orogastric device 100 may be connected via the first channel orifice 923 to an existing feeding machine and via the second channel orifice 924 to a dedicated device having the controller 106 and the pump assembly 105.

Optionally, in order to maintain the sterilization of the pump assembly 105, cable which connected to the second channel orifice 924 includes a filter which filters air conducted via the air channel 914. In such an embodiment, if the elastic esophageal body 103 and/or the air channel which conducts air thereto are torn or perforated, GI fluids, germs, or other impurities are blocked from contaminating the pump assembly 105 and/or a tube that connects the pump assembly 105 to the filter. It should be noted that such a cable allows using the pump assembly 105 for a number of patients without requiring redundant sterilization processes. Optionally, in order to maintain the sterilization of the feeding unit, filter that controls the direction of feeding via the feeding channel 913. In such an embodiment, if the feeding channel 913 is torn or perforated, GI fluids, germs, or other impurities are blocked from contaminating the feeding unit or a tube that connects the feeding unit to the filter.

Optionally, the caps 930, 931 are detachably connected to the exemplary connector 920. In FIGS. 10A and 10B, the caps 931, 930 are not connected to the connector 920 but rather supported by a holding element 932, such as a flexible band. By placing them in front of the orifices of the exemplary connector 920, sterilization is maintained.

It is expected that during the life of a patent maturing from this application many relevant devices and methods will be developed and the scope of the term biological biocompatible material is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for use with enteral feeding, comprising:
    an elongated body having a length configured for insertion along an esophagus of a patient into a stomach of the patient;
    a plurality of electrodes located along the length of the elongated body and positionable for placement at least within at least one of the stomach and the esophagus;
    a controller in electrical communication with the plurality of electrodes;
    wherein the controller is configured to measure conductivity or impedance between the plurality of electrodes, and
    wherein the controller is configured to detect a gastric fluid in proximity to the plurality of electrodes based on the measured conductivity or impedance and to instruct a pump assembly to:
    inflate an elastic esophageal body mounted to be disposed above a lower esophageal sphincter of the patient when a tip of the elongated body is in the stomach when a gastric fluid is detected in proximity to the plurality of electrodes based on the measured conductivity or impedance, and
    deflate the elastic esophageal body when the gastric fluid is not detected in proximity to the plurality of electrodes based on the measured conductivity or impedance.

2. The apparatus of claim 1, wherein the controller controls a feeding pump in response to the detection.

3. The apparatus of claim 1, wherein the elongated device comprises a feeding tube.

4. The apparatus of claim 1, wherein at least some of the plurality of electrodes are located near or at a distal tip of the elongated body.

5. The apparatus of claim 1, wherein the controller is further configured to determine a location of the elongated body within a subject based on the conductivity or impedance measured between the plurality of electrodes.

6. The apparatus of claim 1, wherein the controller is further configured to measure the conductivity or impedance via a current introduced between the plurality of electrodes.

7. The apparatus of claim 1, wherein the plurality of electrodes are made of a conductive material disposed along an outer surface and in proximity to a distal portion of the elongated body.

8. The apparatus of claim 1, wherein the conductive material comprises at least one member selected from a group consisting of steel, stainless steel, brass, copper, platinum, silver, gold, aluminum alloy, zinc, nickel, tin, magnesium alloy, bronze, phosphor bronze, and conductive polymers.

9. The apparatus of claim 1, wherein the plurality of electrodes are a plurality of wires placed along the elongated body.

10. The apparatus of claim 1, wherein the controller is configured to detect when gastric fluid is in touch with the plurality of electrodes based on the measured conductivity or impedance.

11. A method of detecting gastric fluid, comprising:
   introducing elongated body having a length along an esophagus of a subject into a stomach of the subject;
   positioning at least some of a plurality of electrodes located along the length of the elongated body and within at least one of the stomach and the esophagus;
   measuring a conductivity or impedance between the plurality of electrodes;
   detecting a gastric fluid in proximity to the plurality of electrodes based on the measured conductivity or impedance;
   instructing a pump assembly to:
      inflate an elastic esophageal body mounted to be disposed above a lower esophageal sphincter of the subject when a tip of the elongated body is in the stomach when gastric fluid in proximity to the plurality of electrodes based on the measured conductivity or impedance, and
      deflate the elastic esophageal body when the gastric fluid is not detected in proximity to the plurality of electrodes based on the measured conductivity or impedance.

12. The method of claim 11, wherein measuring a conductivity or impedance comprising measuring via a controller in electrical communication with the plurality of electrodes.

13. The method of claim 11, wherein positioning further comprises determining a location of the elongated body within the subject based on the conductivity or impedance measured between the plurality of electrodes.

14. The method of claim 11, further comprising feeding the subject via feeding apertures of the elongated body when the feeding apertures are placed in the stomach.

15. The method of claim 11, wherein the at least some of the plurality of electrodes are comprised of a conductive material disposed along an outer surface and in proximity to a distal portion of the elongated body.

16. The method of claim 11, wherein measuring a conductivity or impedance comprises measuring the conductivity or impedance introducing a current from a current source between the plurality of electrodes.

17. The method of claim 11, wherein detecting a gastric fluid in proximity to the plurality of electrodes comprises detecting when gastric fluid is in touch with the plurality of electrodes based on the measured conductivity or impedance.

* * * * *